United States Patent [19]

Restaino et al.

[11] Patent Number: 4,689,217
[45] Date of Patent: Aug. 25, 1987

[54] AMINE AND AMMONIUM NITROGEN CONTAINING POLYVINYL ALCOHOL POLYMERS HAVING IMPROVED LIPOPHILIC PROPERTIES FOR USE IN SKIN CONDITIONING, COSMETIC AND PHARMACEUTICAL FORMULATIONS

[75] Inventors: Alfred J. Restaino; Charalambos J. Phalangas; George R. Titus, all of Wilmington, Del.

[73] Assignee: ICI Americas Inc., Wilmington, Del.

[21] Appl. No.: 747,240

[22] Filed: Jun. 21, 1985

Related U.S. Application Data

[62] Division of Ser. No. 540,145, Oct. 7, 1983, abandoned.

[51] Int. Cl.⁴ .................. A61K 7/06; A61K 7/08; A61K 7/021; A61K 7/44
[52] U.S. Cl. .................................. 424/70; 8/405; 8/406; 252/106; 252/107; 424/DIG. 12; 424/59; 424/60; 424/61; 424/63; 424/64; 424/66; 424/68; 424/69; 424/73; 424/78; 514/844; 514/847; 514/969
[58] Field of Search ............... 424/61, 70, 78; 525/56, 525/58, 60, 375, 61; 524/815; 514/844

[56] References Cited

U.S. PATENT DOCUMENTS

| | | | |
|---|---|---|---|
| 2,676,166 | 4/1954 | Webers et al. | 260/85.7 |
| 2,887,469 | 5/1959 | Unruh et al. | 260/77.5 |
| 2,972,606 | 2/1961 | Hartman et al. | 260/91.3 |
| 3,117,951 | 1/1964 | Itoli et al. | 260/91.3 |
| 3,121,607 | 2/1964 | Ohno et al. | 8/115.5 |
| 3,147,233 | 1/1964 | Mendelsohn | 260/29.6 |
| 3,338,883 | 8/1967 | Tesoro et al. | 260/212 |
| 3,348,997 | 10/1967 | Lagally et al. | 162/164 |
| 3,684,784 | 8/1972 | Marze | 260/80.3 N |
| 4,070,530 | 1/1978 | Hobbs | 526/7 |
| 4,182,804 | 1/1980 | Serboli et al. | 525/56 |

*Primary Examiner*—Dale R. Ore
*Attorney, Agent, or Firm*—Richard A. Rowe

[57] ABSTRACT

Polyvinyl alcohol polymers having oxy-linked pendant quaternary ammonium or tertiary amine groups provide a thin film which aids in reducing moisture loss when applied to skin as conditioning lotions or ointments in cosmetic and pharmaceutical formulations.

6 Claims, No Drawings

AMINE AND AMMONIUM NITROGEN CONTAINING POLYVINYL ALCOHOL POLYMERS HAVING IMPROVED LIPOPHILIC PROPERTIES FOR USE IN SKIN CONDITIONING, COSMETIC AND PHARMACEUTICAL FORMULATIONS

This is a divisional of co-pending application Ser. No. 540,145 filed on 10/07/83, now abandoned.

The present invention is directed to skin conditioning polymers which when applied to skin form retentive films which aid in reducing moisture loss. The invention relates in general to film forming polyvinyl alcohol polymer derivatives and specifically to those having certain amine and quaternary ammonium nitrogen containing pendant groups or a combination of these nitrogen containing groups. Of particular interest are polymers having a polyvinyl alcohol backbone or base chain with randomly distributed pendant substituent nitrogen containing groups comprising at least two oxygen linked groups selected from tertiary amines, quaternary ammonium, alkyl, arylalkyl, hydroxy alkyl, alkyl acids and hydroxy alkyl acids.

As a result of the presence of quaternary ammonium groups in the polymer, thin film coatings on animal skin penetrate the outer layers of the skin to provide sufficient adhesive properties while remaining sufficiently elastomeric to avoid discomfort after drying. While the thin films act as a partially impenetrable barrier to prevent loss of moisture by evaporation they also behave as moisture retainers through the possible formation of hydrates at the quaternary ammonium sites and by inclusion of water molecules through hydrogen bonding on the hydrophilic polymer matrix. Other pendant groups on the polyvinyl alcohol chain selected from the tertiary amines and the alkyl groups further enhance the comfort of the dry thin film on the skin while they provide means for adjusting the hydrophilic/lipophilic balance to provide for compatability with specific solvents thereby permitting the polymer to be formulated in a wide number of skin conditioning, cosmetic and pharmaceutical formulations. Furthermore, the polymers act as suspending agents for insoluble pigments and pharmaceutical actives contained in such formulations in high concentrations.

It is an object of the invention to provide for a quaternary nitrogen or tertiary amine containing polyvinyl alcohol polymer base chain (having a number average molecular weight of at least 2,000 and preferably up to about 200,000 and higher when unmodified) and a multiplicity of oxy-linked pendant groups and at least two being selected from the general formulas:

$-R-N^+R_1R_2R_3A^-$,  (a) 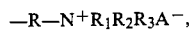

$-R-NR_1R_2$, and  (b) 

$-R_4$  (c) 

wherein
R is alkylene, substituted alkylene preferably hydroxyalkylene, or acylene of formula weight ranging from 14 to about 3,000,
$R_1$, $R_2$, $R_3$ are alkyl or arylalkyl radicals, having 1–20 carbon atoms which may be the same or different,
$A^-$ is an anion,
and $-R_4$ is alkyl, arylalkyl or specific substituents bearing alkyl or arylalkyl radicals such that the total nitrogen content in the resin polymer ranges from 0.01–7.0% by weight. Such polymers have a random selection of (a,b) groups, (a,c) groups, (b,c) groups or (a,b,c) groups. Another object is to provide for a preferred process for the synthesis of such compositions. It is still another object to provide for aqueous solutions containing 0.1–30% by weight of these polymers which are useful in skin conditioning lotions, ointments, cosmetic and pharmaceutical formulations for application to hair, skin and nails. Another object provides for a film forming polymer which also performs as a dispersant for insoluble particulates in such formulations.

R in the above formula may be selected from alkyl groups such as methylene, ethylene, propylene, butylene, pentylene, hexylene, ethylhexylene, dodecylene, tetradecylene, hexadecylene, octadecylene, and substituted alkyl groups such as hydroxypropylene, hydroxybutylene, acetyl, propionyl, butyryl, octadecanoyl, and octadecenyl and their equivalents.

$R_1$, $R_2$, and $R_3$ may be selected from the alkyl groups such as methyl, ethyl, propyl, butyl, pentyl, hexyl, octyl, decyl, dodecyl, tridecyl, tetradecyl, hexadecyl, octadecyl, octadecenyl, phenyl, or benzyl and their equivalents.

$A^-$ may be selected from a large number of anion such as chloride, bromide, iodide, hydroxide, lower alkyl (1–6 carbon atoms) sulfate, tetrafluoroborate, nitrate and perchlorate to name a few.

$R_4$ may be selected from a number of groups such as alkyl, alkylaryl, substituted alkyl and substituted alkylaryl radicals primarily alkyl or arylalkyl radicals bearing hydroxy or carboxyl groups or a combination of hydroxyl and carboxyl groups having a formula weight up to about 3000 and preferably less than 1000. The cumulative formula weight of the pendant groups are controlled in the synthesis of the polymer such that total nitrogen content ranges from 0.01–7% by weight. The overall proportion of $R_4$ groups added to the polyvinyl alcohol base chain are controlled such that their cumulative formula weight comprises from 0.5–50% by weight of the total product polymer weight and the ratio (b/a) of the cumulative formula weight of tertiary amine groups to the total formula weight of quatenary ammonium containing groups may vary from 0–90% by weight. Depending on the amount of the $-R-N^+R_1R_2R_3A^-$ and $-R_4$ groups the presence of $-R-N-R_1R_2$ group may not be needed for certain applications. If the hydroxy or carboxy bearing $-R_4$ type pendant groups are attached to the polyvinyl alcohol base chain prior to the reaction with quatenary ammonium or tertiary amine bearing groups some of the quatenary ammonium or tertiary amine groups may become oxy-linked to the $-R_4$ pendent group in place of being oxy-linked directly to the polyvinyl alcohol base chain.

Specific $R_4$ groups may be selected from methyl, ethyl, propyl, butyl, pentyl, hexyl, octyl, nonyldecyl, dodecyl, tridecyl, tetradecyl, hexadecyl, oxtadecyl, hydroxyethyl, mono or dihydroxypropyl, mono or polyhydroxybutyl, mono or polyhydroxypentyl, mono or polyhydroxyhexyl, mono or polyhydroxyoctyl, mono or polyhydroxypentyl, mono or polyhydroxyhexyl, mono or polyhydroxyoctyl, mono or polyhydroxydecyl, mono or polyhydroxydodecyl, mono or polyhydroxytetradecyl, mono or polyhydroxyhexadecyl, mono or polyhydroxyoxtadecyl, carboxymethylene, carboxyethylene, carboxypropylene, carboxybutylene, carboxypentylene, carboxyhexylene, carboxyheptylene, carboxyoxtylene, carboxydecylene, carboxydodecylene, carboxytridecylene, carboxytetradecylene, carboxypentadecylene, carboxyhexadecylene, carboxyheptadecylene, carboxyoxtadecylene, carboxy(hydroxethylene), carboxy(hydroxypropylene), carboxy(hydroxybutylene), carboxy(hydroxypentylene), carboxy(hydroxyhexylene), carboxy(hydroxyheptylene), carboxy(hydroxyoctylene), carboxy(hydroxydecylene), carboxy(hydroxydodecylene), carboxy(hydroxytridecylene), carboxy(hydroxytetradecylene), carboxy(hydroxypentadecylene), carboxy(hydrohexadecylene), carboxy(hydroxyheptadecylene), and carboxy(hydroxyoctadecylene).

The quaternary nitrogen containing polyvinyl alcohol polymer compositions of the invention may be represented by a typical polymer segment having the following idealized structural formula:

$$-[(-CH_2CHORN^+R_1R_2R_3A^-)(-CH_2CHOH)_{m_1}(CH_2CHOR_4)(CH_2CHOCH)_{m_2}(CH_2CHORN^+-R_1R_2R_3A^-)]-$$

or $$-[(CH_2CHORN^+R_1R_2R_3A^-)(CH_2CHOH)_{p_1}(CH_{m_1}CHORNR_1R_2)(CH_2CHOH)_{p_1}(CH_2CHOR_4-(CH_2CHOH)_{p_3}(CH_2CHORNR_1R_2R_3A^-)]-$$

$m_1$, $m_2 = 0-650$ $m_1 + m_2 = \leq 650$ $p_1$, $p_2$, $p_3 = 0-650$ $p_1 + p_2 + p_3 = \leq 650$ R, $R_1$, $R_2$, $R_3$, $R_4$ and $A^-$ are the same as above.
Illustrative examples of the numerous quaternary and tertiary amine groups and non-nitrogen containing groups in the randomly distributed units is the polyvinyl alcohol base chain may be given as follows:

$$-CH_2CH(OH)CH_2N^+(CH_3)_3Cl^- \quad (1)$$

$$-CH_2CH[CH_2N^+(CH_3)_3Cl^-]O)_eCH_2CH(OH)CH_2N^+(CH_3)_3Cl^- \quad (2)$$

where $e = 1-20$ $$-(C=O)CH_2N^+(CH_2CH_3)_3Br^- \quad (3)$$

$$-CH_2CH(OH)CH_2N^+(CH_3)_2(CH_2Ph)Cl^- \quad (4)$$

$$-CH_2CH_2N^+(CH_3)(CH_2CH_3)(CH_2Ph)CH_3SO_4^- \quad (5)$$

$$-CH[(CH_2)_7CH_3]CH(OH)(CH_2)_7CH_2OH \quad (6)$$

$$-CH[(CH_2)_7CH_3]CH(OH)(CH_2)_7CH_2OCH_2CH(OH)CH_2N^+(CH_3)_3Cl^- \quad (7)$$

$$-CH_2CH[CH_2N^+(CH_3)_3Cl^-]OCH[(CH_2)_7CH_3]CH(OH)(CH_2)_7CH_2OH \quad (8)$$

$$-CH_2CH(OH)CH_3 \quad (9)$$

$$-CH_2CH(CH_3)[OCH_2CH(OH)CH_2N^+(CH_3)_3Cl^-] \quad (10)$$

$$-CH_2CHCH_2N^+(CH_3)_3Cl^-[OCH_2CH(OH)CH_3] \quad (11)$$

$$-CH_2CH(OH)CH_2N(CH_2Ph)CH_3 \quad (12)$$

$$-CH_2CH[OCH_2CH(OH)CH_2N^+(CH_2Ph)CH_3]CH_2N^+(CH_3)_3Cl^- \quad (13)$$

$$-CH_2CH[OCH_2CH(OH)CH_2N^+(CH_3)_3Cl^-]CH_2N(CH_2Ph)CH_3 \quad (14)$$

$$-CH[(CH_2)_7CH_3]CH[OCH_2CH(OH)CH_2N^+(CH_3)_3Cl^-](CH_2)_7CH_2O-CH_2CH(OH)CH_2N^+(CH_3)_3Cl^- \quad (15)$$

$$-(C=O)(CH_2)_{16}CH_3 \quad (16)$$

$$-(C=O)(CH_2)_8CH(CH_2)_7CH_3 \quad (17)$$

$$-(C=O)(CH_2)_7CH=CH(CH_2)_7CH_3 \quad (18)$$

$$-(C=O)(CH_2)_7CH(OH)CH(OH)(CH_2)_7CH_3 \quad (19)$$

where Ph = phenyl radical.

While the above structures serve to illustrate the types of pendant groups which can be added to the polyvinyl alcohol (PVA) base chain it is apparent to one skilled in the art that many other arrangements of similar chemical structure can be added. It has been found that each of the above types of groups used in combination with one or more of the others as a substituent on the polyvinyl alcohol base chain yields the desired combination of products having the right moisture barrier properties especially when the nitrogen content of the final product ranges from 0.01-7% by weight. Depending on the type of radical attached to the nitrogen of the quaternary group the effective range of the nitrogen content could be even more specific. It has been found for example that when the $R_1$, $R_2$. $R_3$, in the above general formulas are all methyl radicals the effective nitrogen content may range from 0.1-5% by weight.

While many techniques have been employed in the art to add substituent groups to vary the polymer change or its hydrophilic-lipophilic balance four preferred methods for attaching the substituent groups to poly-vinyl alcohol involve the reaction of hydroxyl groups of the poly-vinyl alcohol base chain with an epoxy (oxirane) group, a halo-hydrin group in aqueous solution, or a lower molecular weight alkyl alcohol ester of the substituent in a dipolar aprotic solution or an acid halide in either a dipolar aprotic solvent or a two phase system in the presence of an appropriate acid or base catalyst.

While a number of methods may be utilized for the preparation of the PVA derivatives described in this invention, the use of non-aqueous solvents such as dimethyl formamide or similar polar materials is possible, but generally these solvents must be thoroughly removed from the final product. The use of aqueous solvents or mixed aqueous systems if preferable but, in this case, yields must be optimized because of competitive reactions of the quaternary ammonium compounds with water as well as PVA hydroxyls in the presence of catalyst. Improved yields can be obtained by increasing the PVA concentration in water, adding the oxirane compound as a concentrate and reducing to a minimum the amount of base used to catalyze the addition reaction. Salt formed during the reaction is preferentially removed from the final product, since it may have a deleterious effect on the skin moisture barrier properties and its formulation. It has also been found that the pH of the derivatized PVA may affect the skin moisture barrier properties as well as the substantivity to skin. It is generally desirable to work in a pH range between 2–10 preferably from 5–9.

The product can be obtained in a dry form by precipitation, filtering, drying and grinding. The precipitation is accomplished by adding the reaction mixture to a nonsolvent such as acetone, methanol, ethanol and the like. The product also finds use in the form of the aqueous solution or suspension which can preferably be obtained by dialyzing the reaction mass to free it from salts and low molecular weight unreacted intermediates. To obtain a better understanding of the preparative techniques found to be most satisfactory attention is drawn to the following generalized and specific preparations which are intended to illustrate but not limit the invention and wherein all proportions mentioned are based on weight unless otherwise specified.

General Prepartion I

A flask equipped with a water cooled condenser mechanical stirrer and thermometer is charged with polyvinyl alcohol and distilled water to form an aqueous suspension or slurry. The polyvinyl alcohol which is generally a commercially available product prepared by hydrolysis of polyvinyl acetate may have from 0–35% by weight residual acetate groups and preferably from 2–15% by weight. The number avarage molecular weight of the starting material may range from 2,000 up to 200,000 and higher and preferably from 25,000–150,000. In addition and for the purpose of this invention, a polyvinyl alcohol base chain may include up to 25% by weight of another comonomer such as vinylpyrolidone, acrylic and methacrylic acid and esters thereof.

The aqueous slurry is heated to 80°–100° C. and then a catalytic amount of an alkaline hydroxide such as sodium or potassium hydroxide or acidic material when appropriate as a catalyst is added. The solution is then cooled to near ambient temperature if the additon of propylene oxide is intended or 50°–75° C. when fatty epoxides or tertiary amine epoxides are to be added. These reagents may be used either singly or in combination in amounts ranging from 0–0.95 mol per mol of hydroxyl groups on the polyvinyl alcohol chain and preferably from 0.001–0.5 mol per mol of hydroxyl on the base chain. The entire solution is then generally treated with a quaternary ammonium reagent when used at a temperature of 80°–90° C. for a period generally ranging from 3 to 24 hours and preferably from 5 to 10 hours. The quaternary ammonium reagent such as 2,3-epoxypropyltrialkylammoniumhalide or (chlorohydroxypropyl)trimethylammoniumhalide either in aqueous solution or crystalline form may be added either incrementally or all at once and stirred at a temperature of 40°–90° C. and preferably at 60°–70° C. for a period of about 4 hours or until the reaction is complete. These quaternary ammonium halide reagents are typically used in amounts of 0.003–0.95 mol per mol of hydroxyl and preferably from 0.1–0.3 mols per mol of hydroxyl group remaining unreacted on the polyvinyl alcohol base chain.

The reaction mixture is freed from all species below a certain molecular weight by dialysis or ultrafiltration. Two methods may be used, on a static and one a dynamic. In the static method the reaction mixture is placed inside a commercial semi-porous dialysis tube and the tubes are submerged in distilled water typically for periods of 12 to 48 hours. The contents of the tube are then recovered and the product may be used as is or dryed. In the dynamic system a pressure pump is used to move water from the reaction mixture through a semi-porous membrane. The water carries out any inorganics and low molecular weight organics. The resulting concentrated product is then collected and may be used as is in cosmetic formulations or dried by conventional techniques to form a highly disperable solid.

General Preparation II

A flask equipped with a water cooled condenser, mechanical stirrer and thermometer is charged with polyvinyl alcohol and distilled water to form an aqueous suspension or slurry. The polyvinyl alcohol which is generally a commercially available product prepared by hydrolysis of polyvinyl acetate may have from 0–35% by weight residual acetate groups and preferably from 2–15% by weight. The number average molecular weight of the starting material may range from 2,000 up to 200,000 and higher and preferably from 25,000–150,000. In addition and for the purpose of this invention, a polyvinyl alcohol base chain may include up to 25% by weight of another comonomer such as vinylpyrolidone, acrylic and methacrylic acid and esters thereof.

The aqueous slurry is heated to 80°–100° C. and then a catalytic amount of an alkaline hydroxide such as sodium or potassium hydroxide or acidic material when appropriate as a catalyst is added. The entire solution is then generally treated with a quaternary ammonium reagent when used at a temperature of 40°–90° C. for a period generally ranging from 3 to 24 hours and preferably from 5 to 10 hours. The quaternary ammonium reagent such as 2,3-epoxypropyltrialkylammoniumhalide or (chlorohydroxypropyl)trimethylammoniumhalide either in aqueous solution or crystalline form may be added either incrementally or all at once and stirred at a temperature of 40°–90° C. and preferably at 60°–70° C. for a period of about 4 hours or until the reaction is complete. These quaternary ammonium halide reagents are typically used in amounts of 0.003–0.95 mol per mol of hydroxyl and preferably from 0.1–0.3 mols per mol of hydroxyl group remaining unreacted on the polyvinyl alcohol base chain.

The reaction mixture is freed from all species below a certain molecular weight by dialysis or ultrafiltration. Two methods may be used, one a static and one a dynamic. In the static method the reaction mixture is placed inside a commercial semi-porous dialysis tube and the tubes are submerged in distilled water typically for periods of 12 to 48 hours. The contents of the tube are then recovered and the product may be used as is or dryed. In the dynamic system a pressure pump is used to move water from the reaction mixture through a semi-porous membrane. The water carries out any inorganics and low molecular weight organics. The resulting concentrated product is then collected and may be used as is in cosmetic formulations or may be then alkylated in the fashion described in the previous example.

The solution is then cooled to near ambient temperature if the addition of propylene oxide is intended or 50°–75° C. when fatty epoxides or tertiary amine epoxides are to be added. These reagents may be used either singly or in combination in amounts ranging from 0–0.95 mol per mol of hydroxyl groups on the polyvinyl alcohol chain and preferably from 0.001–0.5 mol per mol of hydroxyl on the base chain. A catalytic amount of alkaline hydroxide is used.

To obtain the optimum moisture barrier properties, the resulting solution is then treated by dialysis or ultrafiltration to remove the catalyst, affording an aqueous dispersion that may be used as is or recovered by precipitation.

EXAMPLE 1

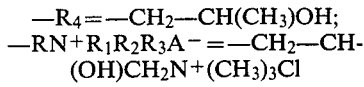

A flask equipped with mechanical stirrer, thermometer, efficient condenser, and dropping funnel was charged with commerical polyvinyl alcohol (88.0 g) and distilled water (500 ml). The PVA contained 2% residual acetate groups and had a number average molecular weight of 126,000. The slurry was heated to 85°-90° C. for one hour and potassium hydroxide (3.0 g in 15 ml H$_2$O) was added. The solution was cooled to 35° C. and propylene oxide (35.0 g) was added dropwise at such a rate to prevent refluxing. When the addition was complete, the temperature was raised to 50° C. for 4 additional hours. The warm solution was then poured into acetone. The precipitate was collected by filtration, washed with acetone and methanol, and dried under vacuum. The yield was 113 g.

This propoxylated polyvinyl alcohol (56.5 g) was then charged to another flask equipped as describe above along with water (500 ml), potassium hydroxide (3.0 g), and (chlorohydroxypropyl)trimethylammonium chloride 80 ml of 48% aqueous solution). The entire solution was then stirred at 60° C. for 16 hours. The product was recovered by precipitation from acetone described previously. The nitrogen content was found to be 0.88%.

EXAMPLE 2

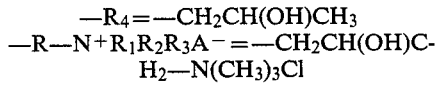

A flask equipped with thermometer, mechanical stirrer, condenser and nitrogen sparger was charged with polyvinyl alcohol (88.0 g, 98% hydrolyzed, MW=126,000) and distilled water (700 ml). Potassium hydroxide (3.0 g in 25 ml water) was added and the pot stirred at 35° C. for one hour. Propylene oxide (58.0 g, 1.0 mol) was then added dropwise. The exotherm was allowed to bring the pot temperature to 55° C. during the addition. When the addition was complete, the temperature was maintained at 55° C. for an additional 4 hours. Recovery was accomplished by precipitation in acetone as described previously. Yield was 134.5 g.

The propoxylated polyvinyl alcohol (72.2 g) was charged to a flask equipped as above along with distilled water (500 ml). The pot was warmed to 55° C. and potassium hydroxide (3.0 grams in 25 ml water) was added. After one hour, 2,3-epoxytrimethylammonium chloride (78 ml of 48% aqueous solution) was added in one slug and the entire solution warmed for an additional 12 hours. Recovery was accomplished by precipitation from acetone as described previously affording a product with a nitrogen content of 1.17%.

EXAMPLE 3

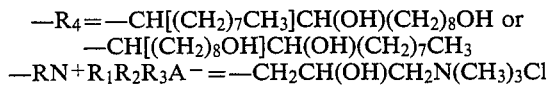

A two liter flask equipped with mechanical stirrer, thermometer and efficient condenser was charged with oleyl alcohol (200 g, 85% purity) and methylene chloride (600 ml) and cooled to 5°-10° C. 3-Chloroperoxybenzoic acid (135 g, 85% purity) and then added through a powder funnel in four equal portions spaced at 20 minutes intervals. The slurry was stirred an additional 3 hours allowing the temperature to rise gradually to ambient. The solution was then filtered and the filtrate extracted with 10% aqueous sodium bicarbonate (3×500 ml) and distilled water (2×500 ml). The organic layer was then collected, dried over anhydrous magnesium sulfate, and concentrated under vacuum to afford a pale yellow oil (212 g, 99% yield) which solidified to a colorless wax on standing. This wax was used without further purification.

A five liter, four necked flask equipped with thermometer, condenser and mechanical stirrer was charged with polyvinyl alcohol (500 g, 98% hydrolyzed, MW=126,000) and distilled water (3700 ml). The slurry was heated to 85° C. and held until dissolution was complete. Potassium hydroxide (31.5 g in 100 ml water) was added and the pot cooled to 70° C. 9,10-Epoxy-octaden-1-ol (235 g, 0.83 mol) was then added and the pot cooled to 70° C. The opaque solution was stirred an additional 3 hours at 60° C. and allowed to cool gradually to ambient temperature.

The resulting latex-like solution was neutralized with a small amount of 6M H$_2$SO$_4$, and bottled. Half of this solution, measured volumetrically, was then charged to similarly equipped three liter flask and warmed to 80° C. Potassium hydroxide (15.0 g in 50 ml H$_2$O) was added and the pot cooled to 60° C. Aqueous chlorohydroxypropylmethylammonium chloride (331.0 ml 48% aqueous solution) was then added all at once. The entire slurry was warmed at 60° C. for an additional 4 hours and recovered by precipitation from acetone.

EXAMPLE 4

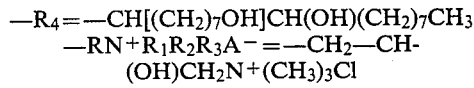

A flask equipped with a mechanical stirrer, thermometer, and condenser was charged with polyvinyl alcohol (44.0 g, 98% hydrolyzed, MW=126,000) and water (400 ml). The pot was heated to 85° C. for one hour and cooled to 80° C. Potassium hydroxide (3.0 g in 15 ml H$_2$O) was added and the pot was cooled to 60° C. Glycidyltrimethylammonium chloride (75.8 g) was then added, and the resultant solution stirred for 5 additional hours. The product was recovered by precipitation from acetone (1500 ml) as previously described. The yield was 110 grams and the nitrogen content was 4.66%.

This quarternized polymer (40.0 g) was then charged to a similarly equipped flask with water (400 ml). The pot was heated to 60°-65° C. and potassium hydroxide (2.0 g in 5 ml H$_2$O) was added. 9,10-Epoxyoctadecanol (8.5 g), prepared as described in Example 3, was added and the solution was stirred at 60° C. for 16 hours. The product was then recovered from acetone and had a nitrogen content of 0.97%.

EXAMPLE 5

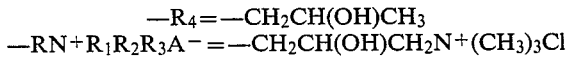

A flask equipped with a mechanical stirrer, condenser, thermometer, and dropping funnel was charged with 44.0 g polyvinyl alcohol (100% hydrolyzed, MW=78,000) and water (400 ml). The solution was warmed to 85°-90° C. and sodium hydroxide (2.6 g in 20 ml $H_2O$) was added. The solution was then cooled to 30° C. Propylene oxide (15.0 g) was added all at once. The solution was stirred one hour at 30° C. and warmed to 70° C. 9,10-Epoxyoctadecanol (10.0 g) was then added along with glycidyltrimethylammonium chloride (30.0 g). The entire solution was then stirred at 70° C. for 3 hours, cooled to ambient temperature, and allowed to stand overnight. The product was recovered by precipitation in methanol.

EXAMPLE 6

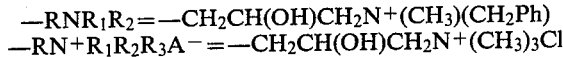

A flask equipped as described in Example 5 was charged with polyvinyl alcohol (44.0 g) and water (400 ml) and heated to 85° C. After one hour, potassium hydroxide (3.1 g in 15 ml $H_2O$) was added and the pot cooled to 65° C. Glycidyltrimethylammonium chloride (30.0 g) was added all at once and the pot was stirred for one hour. Benzyl-(2,3-epoxypropyl)-methylamine was then added dropwise over a 30 minute period and the entire solution was stirred an additional 3 hours. The product was precipitated from methanol/acetone mixture to afford 62 g. The nitrogen content was 1.20%.

EXAMPLE 7

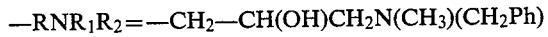

A flask equipped with a mechanical stirrer, thermometer, dropping funnel and condenser was charged with polyvinyl alcohol (44.0 g) (98% hydrolyzed, MW=126,000) and water (400 ml). The slurry was warmed to 90° C. for one hour and potassium hydroxide (3.0 g in 15 ml $H_2O$) was added. The solution was cooled to 75° C. and freshly distilled benzyl-(2,3-epoxypropyl)-methylamine (44.3 g) was added dropwise over a 30 minute period. The entire solution was stirred 3 additional hours at 60°–65° C. and recovered from acetone. The yield was 49.0 g and the nitrogen content was 0.25%.

EXAMPLE 8

A flask equipped as described in the general example is charged with polyvinyl alcohol 44.0 g (MW=86,000, 100% hydrolyzed) and water (400 ml) and heated to 85°–90° C. A catalytic amount of aqueous potassium hydroxide is added and the pot cooled to 70° C. Then 9,10-epoxyoctadecan-1-ol (14.2 g, 0.05 mol) is added and the entire slurry stirred for 3 hours, while gradually cooling to 60° C. Crystalline 2,3-epoxypropyltrimethylammonium chloride (151.5 g, 1.0 mol) is then added and the reaction mixture stirred 4 additional hours at 60° C. The product may then be recovered by precipitation or ultrafiltration to afford a product with a nitrogen content of 5.5% at an approximated yield of 84%.

EXAMPLE 9

Another reaction done as described above except that the 2,3-epoxypropyltrimethylammonium chloride is reduced (75.8 g, 0.50 mol) should afford a product with a nitrogen content of 4.5% based on a reaction yield of 80%.

EXAMPLE 10

A flask equipped as described in Example 5 may be charged with polyvinyl alcohol and distilled water. The aqueous slurry is heated to 80°–90° C. and held for one hour or until the polymer is completely dispersed or solvated. A catalytic amount of an acid such as sulfuric acid or any proton acid or Lewis acid or aluminum hydrosilicate is added and the pot cooled to 40°–90° C. At this point 9,10-epoxyoctadecanol is added and the reaction mixture is stirred for one hour. 2,3-Epoxypropyltrialkylammonium halide can then be added incrementally or all at once. These two epoxides combined may be used in 0.05–1.0 mol ratio preferably from 0.1–0.3 mol per mol of hydroxyl group on the polyvinyl alcohol base chain. The entire mixture is then stirred for an additional period typically 4 hours at 60° C. The product may then be recovered by one of the methods described.

Example 11 illustrates the effect of the salt formed by HCl neutralization on the skin moisture barrier properties. Note the substantial improvement of results based on the final dialyzed product.

EXAMPLE 11

A flask equipped as described in the general example was charged with polyvinyl alcohol (44.0 g, MW=86,000, 100% hydrolyzed) and water (400 ml) and heated at 85°–90° C. for one hour. The vessel was cooled to 80° C. and potassium hydroxide (5.6 g in 15 ml $H_2O$) is added. The vessel was cooled to 60° C. over one hour and 3-chloro-2-hydroxypropyltrimethyl ammonium chloride (18.8 g) was added. The solution was stirred four hours at 60° C. and dialyzed through a semi-porous membrane for five days. The nitrogen content was 0.15%. Improvement in product yields and a significant reduction in reaction time is achievable by using the oxirane derivative followed by addition to a concentrated PVA solution.

The solution was then placed in a flask equipped as described in the general example and heated to 80°–85° C. Potassium hydroxide (0.56 g in 10 ml $H_2O$) was added and the solution stirred for one hour. While cooling to 60° C., 9,10-epoxyoctadecan-1-ol (10.2 g) was added and the entire solution was stirred at 60° C. for three hours. The resulting white dispersion was then split volumetrically into two aliquots. Solution A was neutralized with a small amount of concentrated HCl. This product was found to reduce the transpiration of water through the paper barrier by 42%. Solution B was dialyzed through a semi-porous membrane for 48 hours to pH=7.9. This product was found to reduce the transpiration of water through the paper barrier by 83%.

Moisture Barrier Test On Paper

While the modified polyvinyl alcohol polymers of the invention are best tested for retentivity, substantivity and moisture barrier film forming properties on living animal skin an indication of their effectiveness as a moisture barrier can be obtained by testing on filter paper. In the test results listed in the following Table 1 a 2.5 inch circle of number 1 Whatman filter paper was treated with aqueous solutions containing from 5–10% by weight of modified polymer as described in the examples to obtain a polymer film deposit amounting to about 0.1 gram when dried at room temperature. The test is carried out by taking about 2 grams of aqueous solution of the modified polymer and dropping it over a water wet circle of filter paper from one side. The saturated paper is permitted to dry overnight at room temperature and weighed. Depending on the concentration of solution the procedure may be repeated until the weight pickup is about 0.1 gram so that each filter paper is treated with substantially an equal amount of polymer. The dry paper is sealed over the opening of a test cell containing 100 grams of water and permitted to stand for 100 hours in a constant humidity and temperature room at 70° F. at 40% relative humidity. The weight of water passing through the paper under these conditions is measured by weighing the amount of water remaining in the test cell. Each test employs a control cell containing the identical paper having no polymer treatment. Considering the weight loss through untreated paper as 100 the test results which are listed as percentage reduction in evaporation of water are calculated from the water remaining in the cell. The paper test results provide a rough indication of effectiveness as a moisture barrier for further testing on animal skin.

The materials prepared according to Examples 1 through 7 when screened with the above described moisture barrier test on paper indicate a percent reduction in evaporation measuring from 35 to about 50% which compare favorably with the 40-50% obtained with unmodified polyvinyl alcohol films. Of these, the product of Example 3 gave a result of 48% reduction.

In-vitro tests on animal skins having 5 weight percent of the modified polyvinyl alcohol polymers of this invention indicate comparable results with regard to water vapor transmission (WVT) on Neo-Natal Rat Stratum Corneum when compared with unmodified polyvinyl alcohol films. For example, when corneum membrane having a 5% film polymer as made according to Example 3 is tested, a 72.2% reduction in transmission is obtainable when compared with unmodified PVA (molecular weight of 126,000) having a 66.7% reduction.

Such films can be applied to skin surfaces without detrimental affect upon elasticity. For example, the composition of Example 3 when applied to pigskin at a 5% film loading and thereafter subjected to thermomechanical analysis provides a value of 11.4 while when compared with petroleum jelly which produces maximum elasticity gives a value of 28 units.

The polymers of this invention can be varied over a wide range to control the film forming properties and the formulation properties which are affected by the molecular weight of the PVA, the level of quaternary nitrogen, and the concentration of lipophilic groups attached to the PVA backbone. The exact hydrophile/lipophile ratio to achieve a balance of moisture retention, film properties, skin retention, wash off and formulation properties for these polymers is determined experimentally. In general those derivatized PVA polymers that contain high ratios of polyalkylene to quaternary groups in the side chain are more lipophilic and less moisture sensitive, whereas, those compositions containing higher levels of nitrogen containing side groups tend to be more hydrophilic in character and lend themselves more readily for formulation in systems containing higher levels of water, glycerine or other hydrophilic molecules. There is no upper limit to the molecular weight of PVA that can be used to compare the polymers of this invention. In general it is found that above a molecular weight of several thousand, PVA film properties are sufficiently good to afford functional products. The film properties of PVA above 200,000 are excellent and may be used in the practice of this invention. However, practical limitations on availability of such starting materials and higher working viscosities make these materials somewhat less attractive.

Certain products of this invention may be polymeric surfactants in addition to moisture barriers and may be formulated in a variety of compositions with or without the addition of lower molecular weight surfactants. The choice of the surfactant depends on the specific formulation and properties desired and will depend on the molecular weight of the PVA, the level of quaternary nitrogen, the ratio of lipophilic side chain in the composition and the level of oil or water desired in the final formulation. With these experimental parameters and guidelines it is possible to prepare formulations which afford utilization of the polymers of this invention in a variety of applications including soap formulations, skin care products, vehicles for cosmetic formulations including pigments, powders, dyes, etc. useful in eye shadows, lotions and make-up. The products of this invention may also be used as vehicles for the inclusion of biocides, germicides, sunscreens and other biologically or chemically active molecules in film or particle form to protect burned skin from loss of moisture or infection.

The use of unmodified polyvinyl alcohol polymer in film forming ointment bases and barrier creams for use in protecting the skin against the action of external irritants has met with only limited success (J. B. Ward and G. J. Sperandio, "American Perfumer and Cosmetics" Volume 79, pages 53–55 (1964)). Film forming creams are difficult to produce with polyvinyl alcohol since they are either very difficult to formulate because of their poor mixing characteristics or they form poor films. Lotions and creams made with polyvinyl alcohol in general lack elegance, that is, the in-vitro films made from ointments and lotions containing about 15% polyvinyl alcohol are either slow drying, become greasy and tacky and eventually leave a film which is hard and leathery. Furthermore, good PVA moisture barrier films usually are very hard to remove from the skin because they are difficult to remove with soap and water.

The problems associated with employing unmodified PVA in film forming bases are substantially overcome by the compositions of this invention in that they are easily dispersible in water are compatible with typical lotion formulations, and when applied to the surface of the skin, they dry quickly to form an elastic, smooth pellicle which retains its integrity over long periods of time and is easily removed with soap and water. Tests for cosmetic elegance is accomplished by applying typical moisture barrier lotion formulas to the back of the hand and making observations with respect to ease of application, feel on the skin, time of drying, durability of the film, ease of removal and a host of subjective factors. In most instances, the formulations evaluated do not adversely effect the film forming characteristics of the modified polyvinyl alcohol compositions of this invention. The aqueous moisture barrier compositions of the invention generally have a lotion consistency and may be in the form of oil-in-water or water-in-oil emulsions with the former being preferred because of their more pleasing cosmetic properties. The lotions are preferably made by first preparing the oil phase then preparing the water phase and thereafter adding the water phase to the oil phase. Usually the aqueous phase materials are heated to a temperature of about 75° to about 100° C. and then added slowly with stirring to the oil phase which is heated to about the same temperature.

The oil phase components may contain a variety of materials including emulsifiers, emollients, oils, waxes, perfumes, lanolins, polyalkylenes, sterols and the like.

Water phase components may contain many different materials which include humectants, modified PVA mosisture barrier components of the invention, proteins and polypeptides, preservatives, alkaline agents, thickening agents, perfumes, stabilizers and antiseptics.

The skin conditioning lotions and ointments of the invention contain as an essential ingredient from 0.1–15% by weight and preferably from 0.5–5% by weight of the above described modified polyvinyl alcohol polymers of the invention when used as cosmetics and pharmaceutical compositions. They may be added as aqueous compositions or as dry powder.

The lotions may contain an emulsifier in an amount of from about 0.5 to about 8% and preferably from about 0.25 to about 5% to emulsify the oil components. Typical emulsifiers are selected from the group consisting of polyethoxylated fatty acids having less than about 30 mols of ethylene oxide per mol of fatty acid, ethyoxylated esters, unethoxylated sugar esters, polyoxyethylene fatty ether phosphates, fatty acid amides, phospholipids, polypropoxylated fatty ethers, acyllactates, polyethoxylated polyoxypropylene glycols, polypropoxylated polyoxyethylene glycols, polyoxyethylene, polyoxypropylene ethylene diamines, soaps and mixtures thereof.

Examples of such emulsifiers include polyoxyethylene (8) stearate, myristyl ethoxy (3) myristate, myristyl ethoxy (3) palmitate, methyl glucose sesquistearate, sucrose distearate, sucrose laurate, sorbitan monolaurate, polyoxyethylene (3) oleyl ether phosphate, polyoxyethylene (10) oleyl ether phosphate, lauric diethenyl amide, stearic monoethyl amide, lecithin, lanolin alcohol propoxylates, sodium stearoyl-2-lactate, calcium stearoyl-2-lactate, and the Pluoronics ® offered by BASF Wyandotte. Soaps such as alkaline metal or triethanolamine salts of long chain fatty acids which include sodium stearate, triethanolamine stearate and similar salts of lanolin fatty acids. A preferred emulsifier is polyoxyethylene (21) stearyl ether.

The lotion formulations may contain an emollient material in an amount ranging from 0.2 to 25% and more often 1 to 8% by weight. One function of the emollient is to ensure that the modified polyvinyl alcohol polymer is classified sufficiently to allow it to be in a film-like state on the surface of the skin. Typical emollients are selected from the group consisting of fatty alcohols, esters having fewer than about 24 carbon atoms (for example, isopropylpalmitate), branch chain esters having greater than about 24 total carbon atoms (for example, cetearyl octonate), squalane, liquid or solid paraffins, mixtures of fatty acids and squalane, mixtures of fatty acids and liquid or solid paraffins and mixtures thereof. Typical alcohols and fatty acids which are useful include those having from 12 to 22 carbon atoms such as cetyl alcohol, myristyl alcohol, stearyl alcohol, stearic acid and palmitic acid. Paraffins include, for example, mineral oil, petrolatum and paraffin wax.

The lotions and ointments are particularly stable and effective when adjusted to a pH of 6–8.

Because of their high amine content some of the polymers of the invention may undergo decomposition in sunlight and air to form products which import an undesirable odor to the formulation. To overcome this there should be incorporated with the polymer a minor portion of a material which will inhibit the formation of such decomposition products. These inhibitors/antioxidant materials include nordihydroguaretic acid, citric acid, ascorbic acid, hydroquinone, butylated hydroxy anisole, butylated hydroxytoluene, and any other suitable antioxidant.

The following formulations will serve to demonstrate but not limit the formulations containing the modified polyvinyl alcohol film forming moisture barrier polymer of the invention. Typical lotions contain 0.1–5.0% of the above described modified PVA polymers, 2–5% of an emolient, and 2–5% emulsifier in an aqueous emulsion.

EXAMPLE A

A portion of the aqueous solution prepared according to Example 4 containing 0.5 grams of modified PVA polymer was diluted with water and added to an aqueous solution containing 2.4 grams cetyl alcohol, 1.6 grams stearyl alcohol and 3.0 grams of polyoxyethylene (21) stearyl ether (BRIJ ® 721 surfactant by ICI Americas Inc.). Additional water was added to bring the water concentration to 92.5%. After stirring for about five minutes at 75° C. the emulsion is permitted to cool to room temperature and stored. The lotion was tested subjectively for cosmetic elegance by applying the product to the back of the hand and arm. It was determined to have smooth, silky feel, drying time of less than 15 minutes and a film durability in excess of two days. Residual films and lotions are easily removed from the skin with soap and water.

As mentioned above the polymers of the invention had advantageous cosmetic properties that permit them to be used in preparing cosmetic formulations either as ready to use compositions or concentrates which have to be diluted before use. Therefore, the cosmetic formula may contain the modified polyvinyl alcohol polymers in concentrations ranging from 0.01–15% by weight. The solution of these polymers are particularly useful when they are applied to hair, either alone or with other active substances during a treatment such as shampooing, dyeing, setting, blow drying, permanent waving, etc. They may improve notably the quality of the hair. When employed in hair treatment they facilitate untangling of wet hair and do not remain on dry hair as a sticky residue. In some instances they are expected to give dry hair additional life, a soft feel, a glossy appearance and resistance to tangling.

Hair treating formulations containing dilute aqueous, alcohol or dilute alcohol solutions of the modified polyvinyl alcohol polymer can be employed. Furthermore, they may be employed as creams, lotions, gels or as aerosol sprays. They may be used in combination with perfumes, dyes, preserving agents, sequestering agents, thickening agents, emulsifying agents, etc.

EXAMPLE B

A typical hair rinse formulation containing 5 grams of the modified polymer of Example 8, 7 grams cetyl alcohol, 3 grams of a linear polyoxyethylenated $C_{10}$–$C_{18}$ fatty alcohol, 2 grams of a casein derivative, 0.5 grams tetradecyltrimethylammonium chloride and 82.5 grams of water and a minor amount of hair dye can be used to treat hair having improved looks and anti-static properties.

EXAMPLE C

A typical oxidation hair dye solution containing a 2.5 gram of the modified polymer of Example 9, 10 grams benzyl alcohol, 20 grams oleic acid, 3 grams polyoxyethylene (30), oleo cetyl alcohol, 7 grams oleic diethanolamide, 7.5 grams 2 octyldodecanol, 2.5 grams triethanolamine lauric sulfate, 10 grams ethanol, 18 millileters aqueous ammonium, 1 gram n,n-bis(2-hydroxyethanol)paraphenylenediamine, 0.4 grams resorcin, 0.15 grams m-aminophenol, 0.4 grams alphanaphthol, 0.1 grams hydroquinone, 0.24 grams ethylene diamine tetracetic acid, 1 milliliter sodium bisulfite, and water sufficient to make 100 grams is a typical ammonia oil composition for use as an oxidation hair dye when 130 grams of the solution is mixed with 30 grams of hydrogen peroxide bleach. After hair is treated with the material and allowed to stand for 30–40 minutes and thereafter rerinsed the hair is expected to untangle easily and have a silky touch.

The modified polyvinyl alcohol compositions of the invention may be employed to improve the elegance and stability of personal care products such as liquid and bar soaps, shaving creams, bath products, antiperspirants, sunscreens, cleansing creams and as a suspending agents for insoluble pigments and pharmaceutical actives. Improvement is generally realized when from 0.5-5% by weight of the compositions of this invention are employed in conventional formulations as hereinafter exemplified.

EXAMPLE D

A portion of the aqueous solution prepared according to Example 3 containing 0.5 grams of fatty alcohol modified quaternized PVA was diluted with water and added to an aqueous solution containing 4.0 grams stearic acid, 2.0 grams polyoxyethylene (15) stearyl ether (ARLAMOL ® E by ICI Americas Inc.), 5.0 grams glycerol monostearate and polyoxyethylene stearate (ARLACEL ® 165 by ICI Americas Inc.), and 10.0 grams of 70% sorbitol solutin (SORBO ® by ICI Americas Inc.). After stirring for about 5 minutes at 75° C. the emulsion is permitted to cool to room temperature and stored. The lotion was tested subjectively for cosmetic elegance by applying the product to the back of the hand and arm, was determined to have smooth, silky feel, drying time of less than 15 minutes and a film durability in excess of 2 days. Residual films and lotions are easily removed from the skin with soap and water.

EXAMPLE E

Roll-On Antiperspirant

| Ingredient | % W/W |
|---|---|
| Example 3 | 4.0 |
| polyoxyethylene (21) stearylether | 0.76 |
| polyoxyethylene (2) stearylether | 3.24 |
| water (deionized) | 34.76 |
| Dowicil 200 ®, Dow Chemical | 0.1 |
| Al Zr tetrachlorohydrex-Gly, Rezol 36G, Reheis | 57.14 |

EXAMPLE F

Aerosol Shave Cream

| Ingredient | % W/W |
|---|---|
| Example 3 | 5.0 |
| Cetyl alcohol | 4.3 |
| polyoxyethylene (21) stearylether | 2.2 |
| sorbic acid | .17 |
| water | 74.9 |
| fragance | .08 |
| water | 13.35 |

EXAMPLE G

Oil-in-water Sunscreen Lotion

| Ingredient | W/W % |
|---|---|
| mineral oil | 18.8 |
| cetyl alcohol | 5.0 |
| Arlocel 60 ® emulsifier | 2.5 |
| Tween 60 ® emulsifier | 7.5 |
| Amyl para-dimethylaminobenzoic acid | 1.2 |
| Example 4 | 2.0 |
| water | 63.0 |
| Preservative | q.s. |

EXAMPLE H

Water-in-Oil Pigmented Makeup

| Ingredient | W/W % |
|---|---|
| Mineral Oil | 10 |
| Beeswax | 1.5 |
| Cevesin wax | 1.0 |
| Arlacel 186 ® emulsifier | 3.2 |
| Sorbo ® sorbitol | 28.8 |
| TiO$_2$ and other pigments | 20.0 |
| water | 33.5 |
| Example 6 | 2.0 |

EXAMPLE I

Calamine Lotion

| Calamine | 80 gms |
|---|---|
| Zinc Oxide | 80 gms |
| glycerine | 20 mls |
| bentonite magma | 250 mls |
| calcium hydroxide (concentrated aqueous sol.) | 950 mls |
| Example 1 | 50 gms |

What is claimed is:

1. In an improved aqueous hair, skin and nail conditioning composition comprising an oil phase, a water phase and 0.05% to about 8% of an emulsifier wherein the improvement comprising reducing moisture loss with an aqueous solution containing 0.1 to 30% by weight of a quaternary nitrogen modified polyvinyl alcohol polymer having a molecular weight ranging from alcohol polymer having a molecular weight ranging from at least 2,000 up to about 2,00,000 and which comprises a polyvinyl alcohol having oxygen-linked pendant groups selected from the group consisting of at least two groups of the formula (a) R—NR$_1$R$_2$R$_3$A$^-$, (b) —RNR$_1$R$_2$ and (c) —R$_4$ wherein R is selected from the group consisting of alkylene, hydroxy substituted alkylene and acylene radical of formula weight ranging from 14 to about 3,000, $R_1$, $R_2$ and $R_3$ are selected from the group consisting of alkyl and arylalkyl having 1-20 carbon;

$R_4$ is selected from the group consisting of alkyl, alkylaryl, substituted alkyl, alkylaryl or arylalkyl radical bearing hydroxy or carboxyl groups or a combination of hydroxy and carboxyl groups, $A^-$ is an anion, said polymer having a total nitrogen content ranging from 0.01-7.0% by weight.

2. A composition of claim 1 comprising 0.1-5% by weight of said modified polyvinyl alcohol polymer, 2-5% by weight of an emulsifier and 2-5% by weight of an emollient selected from the group consisting of fatty alcohols, fatty acid esters having fewer than about 24 carbon atoms, branched chain esters having greater than 24 carbon atoms, Squalane, liquid and solid paraffins, mixtures of fatty acids and Squalane, mixtures of fatty acids and liquid and solid paraffins.

3. A composition of claim 1 wherein the cumulative formula weights of all $R_4$ groups are from 0.5-50% by weight of said polymer.

4. A composition of claim 1 wherein the ratio of the total formula weights of all $-NR_1R_2$ groups of the total formula weights of all of said $-RN^+R_1R_2R_3A^-$ groups range from 0-90% by weight of said polymer.

5. A composition of claim 1 comprising 0.1-5% by weight of said modified polymer.

6. A composition of claim 1 containing from 0.5-5% by weight of said modified polymer.

* * * * *